United States Patent [19]

Karrer

[11] 4,060,629
[45] Nov. 29, 1977

[54] PHENOXY-PHENOXY-ALKYL-THIONOCARBAMATE COMPOUNDS

[75] Inventor: Friedrich Karrer, Zofingen, Switzerland

[73] Assignee: Ciba-Geigy Corporation, Ardsley, N.Y.

[21] Appl. No.: 715,592

[22] Filed: Aug. 18, 1976

[30] Foreign Application Priority Data

Aug. 22, 1975 Switzerland .................. 10901/75
July 15, 1976 Switzerland .................. 9085/76

[51] Int. Cl.$^2$ .................. A01N 9/12; C07C 153/09; C07C 153/11
[52] U.S. Cl. .................. 424/300; 260/455 A
[58] Field of Search .................. 260/455 A; 424/300

[56] References Cited

U.S. PATENT DOCUMENTS 3,632,631  1/1972  Wright .................. 260/455 A

Primary Examiner—Joseph P. Brust
Assistant Examiner—Robert C. Whittenbaugh
Attorney, Agent, or Firm—Harry Falber

[57] ABSTRACT

New thionocarbamates of the formula

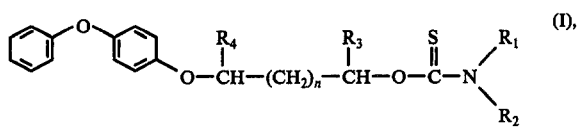

are disclosed, wherein
 $R_1$ represents an alkyl group having 1 to 4 carbon atoms or an alkenyl group having 3 or 4 carbon atoms, each of $R_2$ and $R_3$ represents a hydrogen atom or a methyl group,
 $R_4$ represents a hydrogen atom or
 $R_3$ and $R_4$, if $n$ is 0, together with the carbon atoms to which they are attached form a cyclohexane ring, and
 $n$ is 0 or 1. These compounds are useful as pesticides, especially for the control of insects and pests of the order Acarina and for pest control in the fields of hygiene and storage protection.

11 Claims, No Drawings

PHENOXY-PHENOXY-ALKYL-THIONOCARBAMATE COMPOUNDS

The present invention provides thionocarbamates, a process for their manufacture and a method of using them in pest control.

The thionocarbamates of the present invention have the formula I

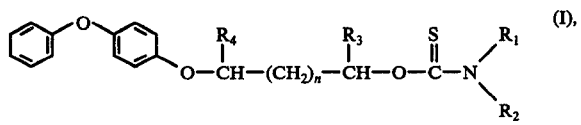

wherein
- $R_1$ represents an alkyl group having 1 to 4 carbon atoms or an alkenyl group having 3 to 4 carbon atoms, each of $R_2$ and $R_3$ represents a hydrogen atom or a methyl group,
- $R_4$ represents a hydrogen atom or
- $R_3$ and $R_4$, if $n$ is 0, together with the carbon atoms to which they are attached form a cyclohexane ring, and
- $n$ is 0 or 1.

The alkyl and alkenyl groups represented by $R_1$ can be straight-chain or branched. Examples of such groups are: methyl, ethyl, propyl, isopropyl, n-butyl, iso-butyl, sec. and tert. butyl, and allyl.

Preferred compounds on account of their action are those of the formula I wherein
- $R_1$ represents a methyl, ethyl or allyl group, $R_2$ and $R_3$ represent a hydrogen atom or a methyl group, but preferably represent a hydrogen atom,
- $R_4$ represents a hydrogen atom and
- $n$ is 0 or 1.

The compounds of the formula I are obtained by methods which are known per se, for example as follows:

A)

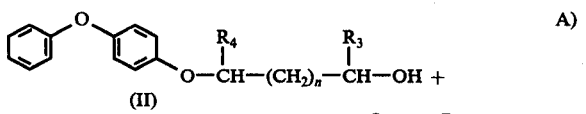

B)

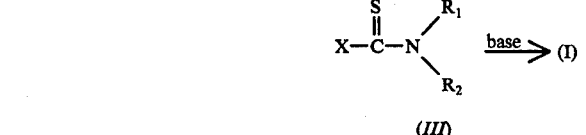

C)

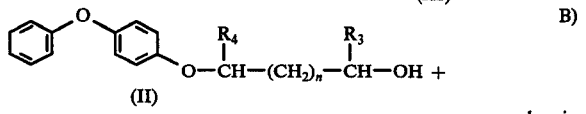

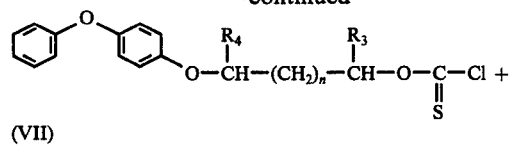

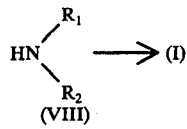

in the formulae (II) to (VIII), the symbols $R_1$, $R_2$, $R_3$, $R_4$ and $n$ are as defined for formula (I) and Z represents halogen, in particular a chlorine or bromine atom.

Examples of suitable bases are tertiary amines, such as trialkylamines. In process B, catalytic amounts of 1,4-diazabicyclo-(2,2,2)octane for example or tertiary amines are added. Processes A, B and C are carried out at a reaction temperature of $-5°$ to $+120°$ C (process A preferably in the temperature range from 10° to 110° C, process B from 10° to 90° C, and process C from 10° to 60° C), at normal pressure and in the presence of inert solvents and diluents.

Examples of suitable solvents or diluents are: hydrocarbons, such as benzene, toluene, hexane, heptane; ethers, such as diethyl ether, dimethoxyethane, dioxane; pyridine, and esters, for example ethyl acetate.

The starting materials of the formulae II and V are known compounds or they can be prepared analogously to known methods described in the literature.

The compounds of the formula I are suitable for combating a variety of animal and plant pests, in particular for combating representatives of the order Acarina of the families: Ixodidae, Argasidae, Tetranychidae, Dermanyssidae, and insects of the families: Acrididae, Blattidae, Gryllidae, Gryllotalpidae, Terrigoniidae, Cimicidae, Pyrrhocoridae, Reduviidae, Aphididae, Delphacidae, Diaphididae, Pseudococoidae, Chrysomilidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Galliphoridae, Trypetidae, Pulicidae. The compounds of formula I are also suitable for pest control in the field of hygiene and of storage protection.

The insecticidal action of the compounds of formula I can be substantially broadened and adjusted to prevailing conditions by adding other insecticides and/or acaricides.

Examples of suitable additives are: organic phosphorus compounds, nitrophenols and their derivatives; formamidines, ureas, carbamates, chrysanthemates and derivatives or chlorinated hydrocarbons.

The compounds of formula I can be used as pure active substance or together with suitable carriers and/or additives. Suitable carriers or additives may be solid or liquid and correspond to the substances conventionally used in the art of formulation, for example: natural and regenerated substances, solvents, dispersing agents, wetting agents, stickers, thickeners, binders or fertilizers.

For application, the compounds of formula I can be processed to dusts, emulsion concentrates, granulates, dispersions, sprays, to solutions or suspensions in formulations well known to those skilled in the art of application.

The compositions of the present invention are obtained in known manner by intimately mixing and/or milling active substances of formula I with the suitable carriers, with or without the addition of dispersants or solvents which are inert to the active substances. The active substances can be applied in the following application forms.

Solid preparations: dusts, tracking agents, granulates (coated granulates, impregnated granulates and homogranulates);

Liquid preparations:
 a. water-dispersible active substance concentrates: wettable powders, pastes or emulsion;
 b. solutions.

The content of active substance in the compositions described above is between 0.1 and 0.1 and 95 percent by weight.

The active substances of formula I can be formulated for example in the following way:

Dusts

The following substances are used for the preparation of (a) a 5% (b) a 2% dust:

(a)

5 parts of active substance
95 parts of talcum (b)

2 parts of active substance
1 part of highly dispersed silicic acid
97 parts of talcum The active ingredients are mixed and milled with the carriers.

Granulates

The following substances are used to obtain a 5% granulate:

5 parts of active substance
0.25 parts of epichlorohydrin
0.25 parts of cetyl polyglycol ether
3.50 parts of polyethylene glycol
91 parts of kaolin (particle size 0.3–0.8 mm).

The active substance is mixed with epichlorohydrin and dissolved in 6 parts of acetone, then the polyethylene glycol and cetyl polyglycol ether are added. The resultant solution is sprayed onto kaolin and the acetone is subsequently evaporated in vacuo.

Wettable Powder

The following ingredients are used to prepare: (a) a 40%, (b) and (c) a 25% and (d) a 10% wettable powder.

(a)

40 parts of active substance,
5 parts of sodium lignin sulphonate,
1 part of sodium dibutyl-naphthalenesulphonate,
54 parts of silicic acid;

(b)

25 parts of active substance,
4.5 parts of calcium lignin sulphonate,
1.9 parts of Champagne chalk/hydroxyethyl cellulose mixture (1:1),
1.5 parts of sodium dibutyl naphthalenesulphonate,
19.5 parts of silicic acid,
19.5 parts of Champagne chalk,
28.1 parts of kaolin;

(c)

25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminum silicate,
16.5 parts of infusorial earth,
46 parts of kaolin;

(d)

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed in suitable mixers with the additives, and the mixture is then milled in appropriate mills and rollers. Wettable powders are obtained which can be diluted with water to give suspensions of any desired concentration.

Emulsifiable concentrates

The following substances are used to produce (a) a 10%, (b) a 25%, and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylarylsulphonate calcium salt,
40 parts of dimethyl formamide,
43.2 parts of xylene;

(b)

25 parts of active substance,
2.5 parts of epoxidised vegetable oil,
10 parts of alkylarylsulphonate/fatty alcohol polyglycol ether mixture,
5 parts of dimethyl formamide,
57.5 parts of xylene;

(c)

50 parts of active substance,
4.2 parts of tributylphenol-polyglycol ether,
5.8 parts of calcium-dodecylbenzenesulphonate,
20 parts of cyclohexanone,
20 parts of xylene.

By diluting these concentrates with water it is possible to obtain emulsions of any required concentration.

Spray

The following ingredients are used to prepare (a) a 5% spray, and (b) a 95% spray:

(a)

5 parts of active substance,
1 part of epichlorohydrin,
94 parts of ligroin (boiling range 160°–190° C);

(b)

95 parts of active substance,
5 parts of epichlorohydrin.

The invention is further illustrated by the following Examples.

EXAMPLE 1

Preparation of 2-[(4-phenoxy)-phenoxy]-ethyl-N-allyl-thionocarbamate

To a solution of 34.6 g of 2-[(4-phenoxy)-phenoxy]-ethanol in 100 ml of anhydrous pyridine is added 0.1 g of 1,4-diazabicyclo(2,2,2)-octane (=DABCO) and 16.8 g of allylisothiocyanate are added dropwise at 70° C with stirring in the course of approx. 1 hour. The reaction mixture is kept for a further 40 hours at 70° C, the pyridine is thereafter distilled off in vacuo and the residue is poured into 400 ml of water while stirring vigorously. The precipitate, which falls out in crystalline form is collected by filtration, dried, and recrystallised from isopropanol to yield 2-[(4-phenoxy)-phenoxy]-ethyl-N-allyl-thionocarbamate with melting point of 96°–97° C.

EXAMPLE 2

Preparation of 2-[(4-phenoxy)-phenoxy]-ethyl-N,N-dimethylthionocarbamate

To a solution of 23.0 g (0.10 mole) of 2-[(4-phenoxy)-phenoxy]-ethanol and 14.2 g (0.14 mole) of triethylamine in 50 ml of toluene are added dropwise 14.8 g (0.12 mole) of diethylthiocarbamoyl chloride and the reaction mixture is stirred for 16 hours at room temperature and subsequently for 47 hours at 120° C. The reaction mixture is worked up by pouring it onto ice-water and then extracting with ether. The ethereal extract is washed once with water and once with a saturated solution of sodium chloride, dried over sodium sulphate and concentrated by rotary evaporation. The residue is crystallised from isopropanol to yield 2-[(4-phenoxy)-phenoxy]-ethyl-N,N-dimethylthionocarbamate with a melting point of 92°–94° C.

The following compounds of the formula I are also obtained in analogous manner:

| structure | physical data |
|---|---|
| 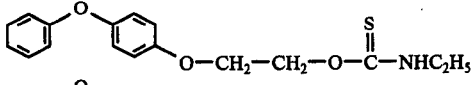 | m.p.: 99° – 101° C |
| 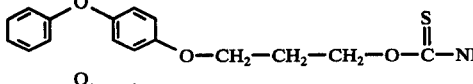 | m.p.: 81° – 82° C |
| 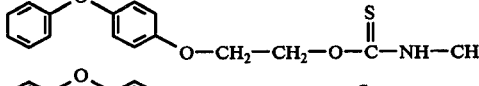 | m.p.: 101° – 103° C |
| 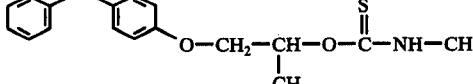 | $n_D^{20}$ 1.5728 |
| 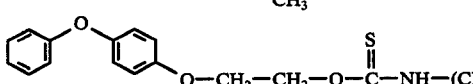 | m.p.: 68° – 69° C |
| 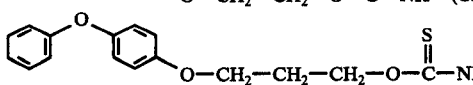 | $n_D^{20}$ 1.5751 |
| 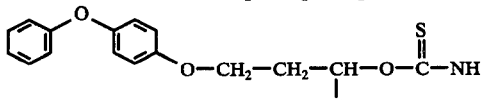 | $n_D^{20}$ 1.5680 |
|  | $n_D^{20}$ 1.5701 |
| 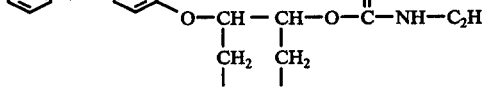 | |

EXAMPLE 3

A. Contact action on Dysdercus fasciatus larvae

A specific amount of a 0.1% solution of active compound in acetone (corresponding to 10 mg active substance/m²) was pipetted into an aluminium dish and distributed homogeneously.

After evaporation of the acetone, 10 larvae of Dysdercus fasciatus in the fifth stage were put into the dishes containing feed and moist cotton wool. The dish was then covered with a perforated top.

After about 10 days, i.e. after the untreated controls had shed and emerged fully to the adult stage, the treated test subjects were examined to ascertain the number of normal adults.

The compounds of formula I displayed good activity in the above test.

B. Contact action on *Tenebrio molitor* pupae

A specific amount of a 0.1% solution of active substance in acetone, corresponding to 10 mg active substance/m², was pipetted into an aluminum dish and homogeneously dispersed.

After evaporation of the acetone, 10 pupae which had just shed their cocoon were placed onto the treated plate. The dish was covered with a perforated top.

After the untreated controls had emerged from the pupae cocoon as imagines, the test subjects were examined to ascertain the number of adults.

The compounds of formula I showed good activity in the above test.

EXAMPLE 4

Action on *Musca domestica*

50 g of freshly prepared CSMA nutrient substrate for maggots were charged into beakers. A specific amount of a 1% acetonic solution of the respective active substance was pipetted onto the nutrient substrate present in the beakers. The substrate was then thoroughly mixed and the acetone subsequently allowed to evaporate over a period of at least 20 hours.

Then 25 one day-old maggots of *Musca domestica* were put into each of the beakers containing the treated nutrient substrate for testing with each active substance at one of its given concentrations. After the maggots had pupated, the pupae were separated from the substrate by flushing them out with water and then deposited in containers closed with a perforated top.

Each batch of flushed out pupae was counted to determine the toxic effect of the active substance on the maggot development. The number of flies which had hatched out of the pupae was then counted after 10 days and any influence on the metamorphosis thereby determined.

The compounds of the formula I displayed good activity in this test.

EXAMPLE 5

Action on the larvae of *Aedes Aegypti*

150 ml of water were put into each of a number of beakers. A specific amount of a 0.1% solution of the active substance in acetone was pipetted onto the surface of the water. After evaporation of the acetone, 30 to 40 two day-old Aedes larvae were put into each of two beakers containing the active substance at one of its concentrations. Ground feed was added to the contents of each beaker, which was covered with a copper gauze top.

Evaluation of mortality was made after 1, 2 and 5 days, regard being had to inhibition of pupation, metamorphosis, and shedding and emergence to the adult stage.

The compounds of the formula I exhibited a good action in this test.

EXAMPLE 6

Action on ticks:

A. *Rhipicephalus bursa*

5 adult ticks and 50 tick larvae were counted into each of a number of test tubes and immersed for 1 to 2 minutes in 2 ml of an aqueous emulsion containing a concentration of 100, 10, 1 or 0.1 ppm of test substance of formula I. The tube was then sealed with a cotton wool plug and placed on its head to enable the cotton wool to absorb the emulsion of the active substance.

The adults were evaluated after 2 weeks and the larvae after 2 days.

B. *Boophilus microplus* (larvae)

20 sensitive and 20 OP-resistant larvae were tested in a dilution series analogous to the one used in test A. (the resistance refers to the tolerance towards diazinone).

The substances of formula I acted in these tests on adults and larvae of *Rhipicephalus bursa* and OP-sensitive and OP-resistant larvae of *Boophilus microplus*.

EXAMPLE 7

Action on eggs of *Spodoptera littoralis*

Eggs of *Spodoptera littoralis* were immersed in a 0.05% solution of active substance in acetone. The treated eggs were then kept in plastic dishes at 21° C and 60% relative humidity. After 3 to 4 days the hatching out rate was determined. Compounds of formula I acted well on eggs of *Spodoptera littoralis* in this test.

What is claimed is:

1. A compound of the formula I

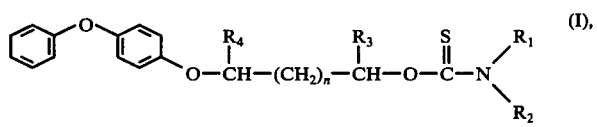

wherein
$R_1$ represents an alkyl group having 1 to 4 carbon atoms or an alkenyl group having 3 or 4 carbon atoms,
each of $R_2$ and $R_3$ represents a hydrogen atom or a methyl group,
$R_4$ represents a hydrogen atom or
$R_3$ and $R_4$, if $n$ is 0, together with the carbon atoms to which they are attached form a cyclohexane ring, and
$n$ is 0 or 1.

2. A compound according to claim 1, wherein
$R_1$ represents a methyl, ethyl or allyl group,
$R_2$ and $R_4$ represent a hydrogen atom,
$R_3$ represents a hydrogen atom or a methyl group, and
$n$ is 0 or 1.

3. A compound according to claim 2, wherein $R_3$ represents a hydrogen atom.

4. The compound according to claim 3 of the formula

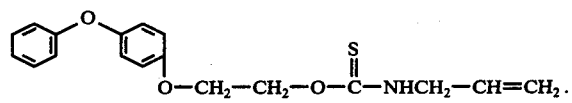

5. The compound according to claim 3 of the formula

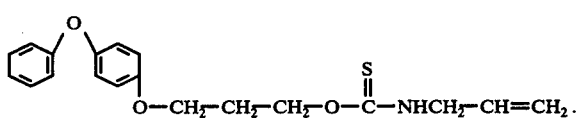

6. The compound according to claim 3 of the formula

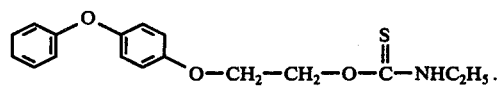

7. The compound according to claim 1 of the formula

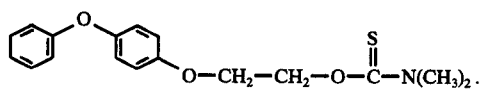

8. An insecticidal and acaricidal composition comprising an insecticidally and acaricidally effective amount of a compound according to claim 1 together with a suitable carrier therefor.

9. A method for combatting insects and acarids which comprises applying to the locus thereof an insecticidally and acaricidally effective amount of a compound according to claim 1.

10. The method of claim 9, wherein in said compound $R_1$ represents a methyl, ethyl or allyl group, $R_2$ and $R_4$ represent a hydrogen atom, $R_3$ represents a hydrogen atom or a methyl group, and $n$ is 0 or 1.

11. The method of claim 10, wherein $R_3$ is hydrogen.